US00PP30283P2

(12) United States Plant Patent
Dirr et al.

(10) Patent No.: US PP30,283 P2
(45) Date of Patent: Mar. 12, 2019

(54) ***VITEX* PLANT NAMED 'BAILTEXONE'**

(50) Latin Name: ***Vitex trifolia* x *Vitex agnus-castus***
Varietal Denomination: Bailtexone

(71) Applicant: Bailey Nurseries Inc, Newport, MN (US)

(72) Inventors: Michael A. Dirr, Bogart, GA (US); Rhonda Helvick, Madison, GA (US); Oren McBee, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 15/732,411

(22) Filed: Nov. 7, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Vitex* plant named 'Bailtexone' that is characterized by its compact, rounded to upright growth habit, its foliage that is olive green in color on the upper surface and light purple in color on the lower surface, its flowers that are violet in color.

2 Drawing Sheets

Botanical classification: *Vitex trifolia* x *Vitex agnus-castus*.

Variety denomination: 'Bailtexone'.

BACKGROUND OF THE INVENTION

The present invention relates to a new and distinct cultivar of *Vitex trifolia*. The new *Vitex* will hereafter be referred to by its cultivar name, 'Bailtexone'. 'Bailtexone' is a new cultivar of chaste tree grown for use as an ornamental landscape plant.

The new cultivar was derived from a controlled breeding program conducted by the Inventors in Watkinsville, Ga. The objective of the breeding program is to develop a new cultivar of *Vitex* that is cold hardy with purple foliage. 'Bailtexone' arose from a cross-made in 2012 between *Vitex trifolia* 'Purpurea' (not patented) as the female parent and unnamed and unpatented plant of *Vitex agnus-castus* as the male parent. 'Bailtexone' was selected as a single unique plant in 2013 from amongst the seedlings derived from the above cross.

Asexual propagation of the new cultivar was first accomplished by semi-hardwood stem cuttings by one of the Inventors in Watkinsville, Ga. in 2014. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailtexone' as a unique cultivar of *Vitex*.

1. 'Bailtexone' exhibits a compact, rounded to upright growth habit.
2. 'Bailtexone' exhibits foliage that is olive green in color on the upper surface and light purple in color on the lower surface.
3. 'Bailtexone' exhibits flowers that are violet in color.

'Purpurea', the female parent of 'Bailtexone', differs from 'Bailtexone' in being hardy in U.S.D.A. Zones 9 to 11; less cold hardy than 'Bailtexone'. The male parent of 'Bailtexone' differs from 'Bailtexone' in being a tree with a much taller plant height and a vase shaped plant habit, and in having compound palmate shaped leaves that are grey-green in color on both surfaces. 'Bailtexone' can also be compared to the *Vitex* cultivar 'PIIVAC-I' (U.S. Plant Pat. No. 25,914). 'PIIVAC-I' differs from 'Bailtexone' in having foliage that is dark green in color and flowers that are blue in color.

BRIEF DESCRIPTION OF THE DRAWINGS

The accompanying colored photographs illustrate the overall appearance and distinct characteristics of the new 'Bailtexone'. The photographs were taken of a 4 year-old plant of 'Bailtexone' as grown outdoors in the ground in Watkinsville, Ga.

The photograph in FIG. 1 provides a side view of 'Bailtexone' in bloom.

Figure 1:
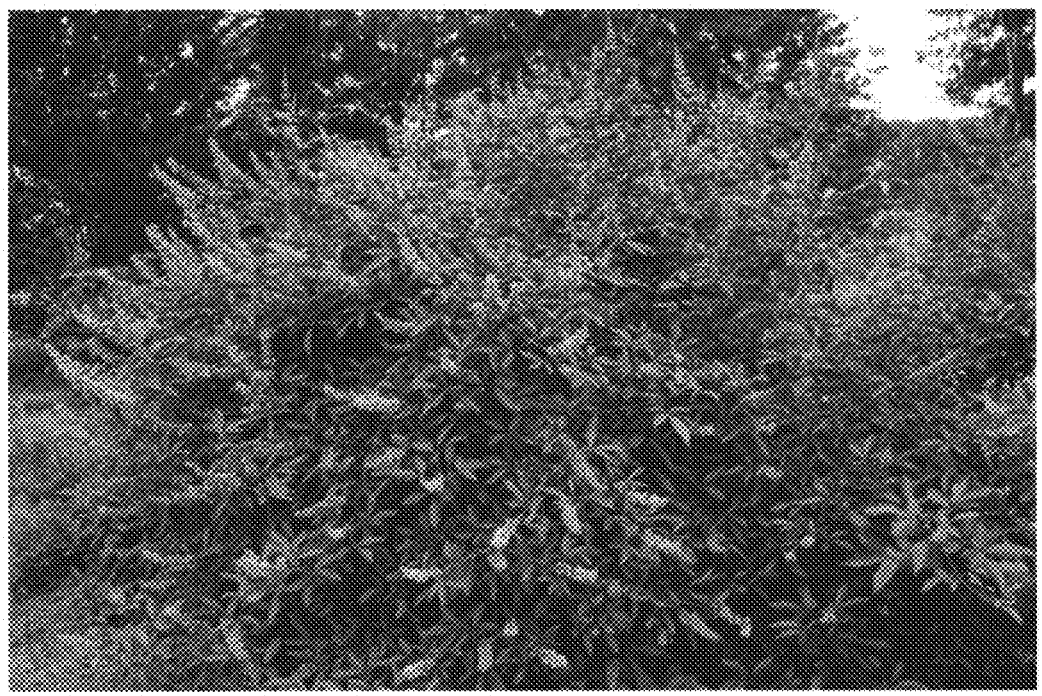
Figure 2:
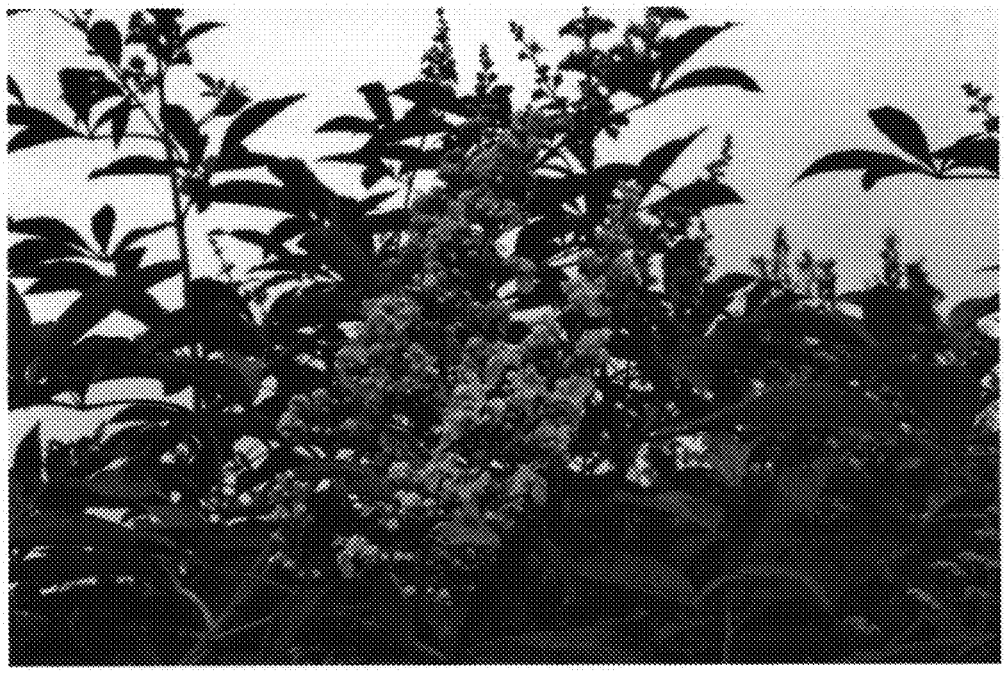

The photograph in FIG. 2 provides a close-up view of the flowers and foliage coloration of 'Bailtexone'.

The colors in the photographs are as close as possible with the photographic and printing technology utilized and the color values cited in the Detailed Botanical Description accurately describe the colors of the new *Vitex*.

DETAILED BOTANICAL DESCRIPTION

The following is a detailed description of 4 year-old plants of the new cultivar as grown outdoors in the ground in Watkinsville, Ga. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—June to September in Watkinsville, Ga.

*Plant type.*—Deciduous flowering shrub.

*Plant habit.*—Compact and rounded to upright plant habit.

*Height and spread.*—An average of 165 cm in height and 182 cm in width as a 3 year-old plant in the landscape.

*Hardiness.*—At least in U.S.D.A. Zones 7 to 9.

*Diseases.*—No susceptibility or resistance to diseases has been observed.

*Root description.*—160A in color, young roots are fibrous, older roots become woody.

*Root development.*—An average of 6 weeks at 32° C. for root initiation and an average of 3 months at 32° C. to produce a young rooted plant.

*Propagation.*—Semi-hardwood stem cuttings.

*Growth rate.*—Vigorous.

Branch description:

*Branch shape.*—Tetragonal on first year growth and round on second year growth.

*Branch color.*—Main and lateral branches; first year; 191A, flushed with N77D, second year; N199B, trunk; N199B.

*Branch size.*—Main branches; first year; 30.8 cm in length, 3 mm in diameter, second year; 66 cm in length, 5 mm in diameter, lateral branches; 85 cm in length, 1.5 cm in diameter, trunk; multi-branched and 4 cm in diameter at soil level.

*Branch surface.*—Main and lateral branches; first year; covered with tomentulose pubescence, second year; glabrous, trunk; fine barked.

*Branch strength.*—Young; flexible and strong, mature; easily broken.

*Branching.*—Freely and multi-branching habit, pruning enhances lateral development, an average of 12 lateral branches on a 4-year-old plant.

*Branch aspect.*—Held at angles ranging between 45° to 75°.

*Internode length.*—An average of 6 cm.

*Vegetative buds.*—Opposite in arrangement, sessile, an average of 1.5 mm in length and 1 mm in width, subglobose in shape, 174A in color, surface has 2 bud scales covered with tomentulose pubescence.

Foliage description:

*Leaf quantity.*—An average of 16 per branch.

*Leaf/leaflet shape.*—Leaf ovate, leaflet elliptic to ovate to lanceolate.

*Leaf/leaflet size.*—Leaf; 6 cm in length and 11 cm in width, leaflet; an average of 6 cm in length and 2 cm in width.

*Leaflet/leaflet arrangement.*—Opposite, palmate.

*Leaflet division.*—Compound with 3 to 5 leaflets.

*Leaflet base.*—Cuneate.

*Leaflet apex.*—Acuminate.

*Leaflet venation.*—Pinnate, upper surface NN137A, lower surface N77D.

*Leaflet margins.*—Entire.

*Leaflet attachment.*—Petiolate.

*Leaflet surface.*—Upper surface; glabrous and glossy, lower surface; tomentulose.

*Leaflet color.*—Young upper surface; 137A, young lower surface; N77C, mature upper surface; NN137A, mature lower surface; N77C.

*Leaflet fragrance.*—A spicy aroma when crushed.

*Petiole/petiolules.*—Average of 3.5 cm in length and 2 mm in diameter, both surfaces tomentulose, upper surface 199A with a hint of N77D, petioles; average of 1.5 cm in length and 2 mm in width, both surfaces tomentulose, upper surface 199A with a hint of N77D.

Flower description:

*Inflorescence type.*—Terminal racemose-panicle.

*Lastingness of inflorescence.*—Inflorescences are showy for an average of 2 weeks, individual flowers last an average of 2 days, self cleaning.

*Inflorescence size.*—An average of 15 cm in height and 6 cm in width.

*Inflorescence number.*—15 to 20 per lateral branch.

*Flower number.*—An average of 250 flowers per inflorescence.

*Flower fragrance.*—Very fragrant.

*Flower buds.*—Obovate in shape, an average of 7 mm in length and 4 mm in depth, surface is glabrous, 91A in color.

*Flower aspect.*—Upright to outward.

*Flower type.*—Bilabiate (one larger petal and one 4-lobed).

*Flower size.*—An average of 1 cm in height and 5 mm in diameter.

*Petals.*—An average of 2, fused at the base to form the corolla tube, tube; an average of 4 mm in length and 2 mm in width, 90B in color on both surfaces, lower petal; cupped, 5 mm in length, 3 mm in width, oblong in shape, broad obtuse to rounded apex, upper and lower surface glabrous, entire margin, upper petal; 4-lobed, each 3 mm in length, and 2.5 mm in width, oblong in shape, broad obtuse to rounded apex, upper and lower surface glabrous, entire margin color both petals; upper surface 90B, lower surface 91B.

*Calyx.*—Consists of 5 fused sepals with acute apices, an average of 5 mm in length and 2 mm in diameter.

*Sepals.*—An average of 5 petals in a single whorl, fused at base, elliptical in shape, entire margins, acute apex, both surfaces are tomentulose, combined an average of 5 mm in length and 2 mm in width, outer surface N187B in color, inner surface 143B in color.

*Peduncles.*—Strong, an average of 5 cm in length and 2.5 mm in diameter, N199B in color, surface is glabrous.

*Pedicels.*—Strong, an average of 5 mm in length and 1 mm in diameter, 85B in color, surface is tomentulose.

Reproductive organs:

*Stamens.*—Stamens; 4 per flower attached to the inner base of the corolla tube, 4 mm in length, glabrous surface, anther N92B in color, filaments 91C in color, pollen is moderate in quantity and 155B in color.

*Pistils.*—1 inferior pistil per flower, an average of 3 mm in length, 1 mm in width, glabrous surface, style; an average of 3 mm in length and 77C in color, stigma; forked, 1 mm in width and 155D in color, ovary; 155D in color and 1 mm in diameter.

*Fruit and seed.*—Drupe; rounded to oblong in shape, 5 mm in length, 4 mm in diameter, immature color 145B and 178B at the apex, mature color N200B, each drupe contains 1 seed that is an average of 4.5 mm in length, 3.5 mm in width, N199B in color.

It is claimed:

1. A new and distinct cultivar of *Vitex* plant named 'Bailtexone' as herein illustrated and described.

* * * * *